United States Patent [19]

Pappas

[11] Patent Number: 6,152,960

[45] Date of Patent: Nov. 28, 2000

[54] FEMORAL COMPONENT FOR KNEE ENDOPROSTHESIS

[75] Inventor: Michael J. Pappas, Jensen Beach, Fla.

[73] Assignee: Biomedical Engineering Trust I, South Orange, N.J.

[21] Appl. No.: 09/227,015

[22] Filed: Jan. 7, 1999

Related U.S. Application Data

[63] Continuation-in-part of application No. 09/170,678, Oct. 13, 1998.

[51] Int. Cl.[7] .......................................................... A61F 2/38
[52] U.S. Cl. ........................................ 623/20.31; 623/20.35
[58] Field of Search ........................... 623/20, 19, 18, 623/20.14, 20.15, 20.21, 20.35, 20.3, 20.31

[56] References Cited

U.S. PATENT DOCUMENTS

| | | |
|---|---|---|
| 4,309,778 | 1/1982 | Buechel et al. . |
| 4,340,978 | 7/1982 | Buechel et al. . |
| 4,470,158 | 9/1984 | Pappas et al. . |
| 4,944,756 | 7/1990 | Kenna . |
| 5,219,362 | 6/1993 | Tuke et al. . |
| 5,556,432 | 9/1996 | Kubein-Messenburg et al. . |
| 5,609,643 | 3/1997 | Colleran et al. ........................... 623/20 |
| 5,702,458 | 12/1997 | Burstein et al. . |
| 5,935,173 | 8/1999 | Roger et al. ............................... 623/20 |

Primary Examiner—V. Millian
Assistant Examiner—Alvin Stewart
Attorney, Agent, or Firm—Anthony J. Casella; Gerald E. Hespos; Michael J. Porco

[57] ABSTRACT

A femoral component of a knee prosthesis includes a bearing surface defined by a smooth, continuous surface which in one embodiment is entirely formed by a series of three segments of surfaces of revolution, the respective shapes of which are generated by rotating a common generating curve around three separate generating axes at respective pairs of major generating radii and through respective angles of rotation. The central segment of the surfaces of revolution constantly maintains the substantially same contact configuration with the superior bearing surface of a bearing insert over a range extending from full extension (0° of flexion) to at least 45° of flexion and up to 105° of flexion. The maintenance of the substantially same contact configuration ensures area, point or line contact between the articulating surfaces which reduces contact stress and wear in flexion. In a second embodiment, the bearing surface is defined by four segments of surfaces of revolution shaped for implantation in a knee where one or both cruciate ligaments are retained.

16 Claims, 7 Drawing Sheets

90 DEGREES OF FLEXION

FULL EXTENSION

FEMORAL COMPONENT FOR KNEE ENDOPROSTHESIS

This application is a continuation-in-part application of U.S. patent application Ser. No. 09/170,678, filed on Oct. 13, 1998, now pending.

BACKGROUND OF THE INVENTION

This invention relates to knee endoprostheses, and, more particularly, to femoral components for knee endoprostheses.

Figure 1:
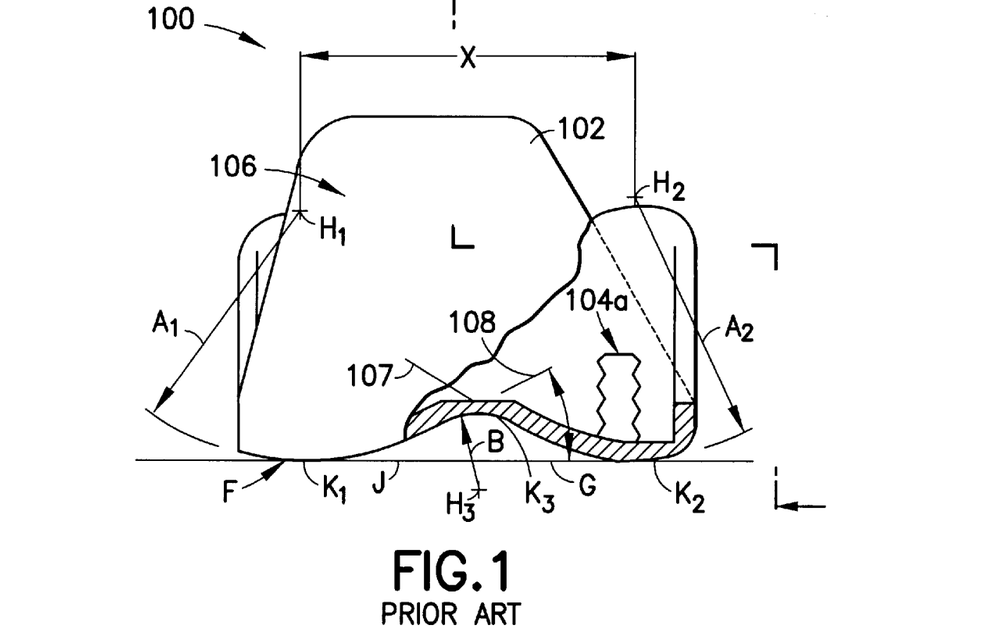
Figure 2:
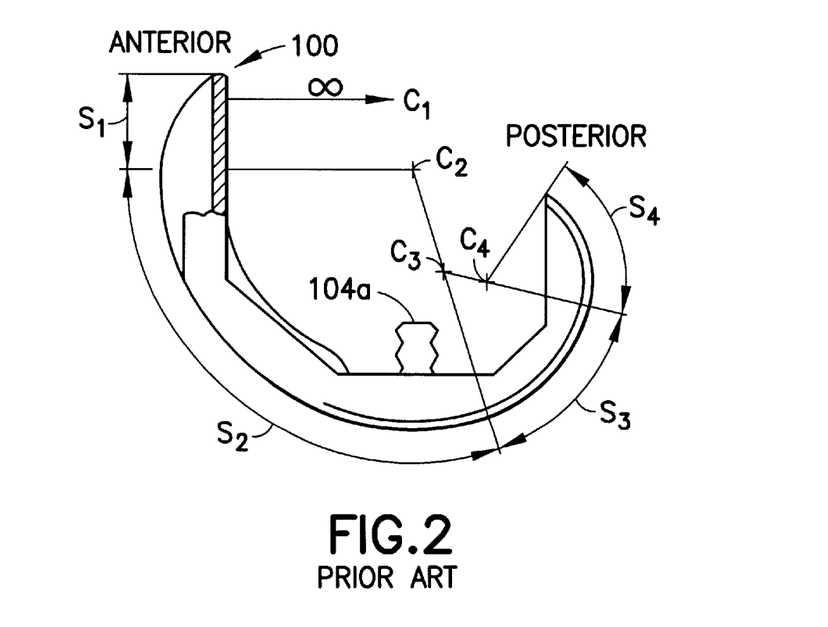

Femoral components having a smooth articulating surface defined by a plane curve rotated about a plurality of axes are known in the prior art. A widely accepted polycentric femoral design in the field of endoprosthetics is disclosed in U.S. Pat. Nos. 4,309,778, 4,340,978 and 4,470,158 which issued to the inventor of the subject application as a co-inventor, and shown in FIGS. 1 and 2. The disclosures of U.S. Pat. Nos. 4,309,778, 4,340,978 and 4,470,158 are incorporated by reference herein for thorough and extensive descriptions of the prior art femoral design. To briefly summarize, referring to FIGS. 1 and 2, femoral component 100 has an outer bearing surface 102 for articulation with a thermoplastic bearing insert and, optionally, a patella component. The bearing surface 102 defines two condyles on the femoral component 100, each being arcuately formed in two coordinate directions. As shown in FIG. 1, a plane curve "F" is defined by arcs K1, K2, and K3, generated respectively about center points H1, H2, and H3 with respective radii A1, A2, and A3 and tangent lines 107, 108 blending respectively arcs K2 and K3, and K1 and K3. Referring to FIG. 2, the plane curve "F" is rotated respectively about axes C1–C4 to respectively generate segments of surfaces of revolution S1–S4 from the anterior portion of the femoral component to the posterior portion. The largest segment S2 is referred to as the primary load bearing surface segment, since the portions of the femoral component corresponding to the segments S2 bear the majority of load during use. The radius used to define the segment S2 from the axis C2, for each of the condyles, is equal to the radius A1, which in turn is equal to the radius A2. It is thus apparent, the segment S2 of each of the condyles of the femoral component is spherically generated about the axis C2. The arcuate length of the segment S2 allows congruent articulation between the femoral component and a bearing insert during use over the range from full extension to approximately 32° of flexion. The bearing insert used with this femoral component is formed with two bearing surfaces, each corresponding to a condyle, and each dimensioned to the spherical dimensions of the segments S2. It can be appreciated, that during the majority of activity by a wearer of the prior art femoral component and bearing insert combination, congruent contact is maintained between the condyles and the bearing surfaces of the bearing insert over the arcuate length of the segment S2. As such, area contact is developed and maintained therebetween during normal activity of a wearer of the prosthesis, such as walking and standing, and stress loading is minimized. Outside the range of congruent contact, incongruent contact is generated resulting in line or point contact. It should be noted that the knee prosthesis described above operates well under incongruent articulation.

Although there are many advantages to the above-described femoral component, there still exists the need for a femoral component which can maintain congruency with a bearing insert over a larger range of flexion than in the prior art.

SUMMARY OF THE INVENTION

A new and improved femoral component is provided which is configured such that there are two articulations which use the same primary load bearing segment and wherein one articulation contact configuration does not change from zero through at least forty-five degrees (45°) of flexion. The subject femoral component is formed by the rotation of a plane curve about at least one axis and preferably a maximum of four axes, and includes a bearing surface with two condyles that are defined by the plane curve. A large segment of each of the condyles is spherically generated about radii lying along a common axis. The spherically generated segments of the condyles are much greater in length as that compared to the segment S2 of the prior art. In use, the largest segment defined by the condyles is disposed to articulate both with a patella component and a bearing insert, wherein substantially the same contact configuration is constantly maintained between the largest segment and the bearing insert over the range from 0° of flexion to at least 45° of flexion and up to approximately 105° of flexion. Consequently, contact stress and wear in flexion are reduced over a much greater range of motion than in the prior art. As an alternative, the substantially same contact configuration can be constantly maintained over a range from 0° of flexion to at least 60° of flexion and up to approximately 105° of flexion.

As used herein, "contact configuration" is the configuration of the two surfaces at the point, line or area of contact without load being applied therebetween. With respect to a knee prosthesis, a "contact configuration" is defined between each pair of contacting surfaces. Natural knees and implanted knee prostheses are subjected to various loadings—the loading being a function of a person's body weight, flexion angles, phase angles, etc. For purposes of this invention, the "contact configuration" defined by contacting surfaces of a knee prosthesis (or other prosthesis) is defined without the loadings described above.

There are two embodiments of the invention disclosed herein. It should be noted, the large change from the prior art in the location of the center of curvature of the contact region of the femoral component of the first embodiment in flexion up to 105° makes this design unsuitable for use with devices which are implanted in knees where a viable posterior and/or anterior cruciate ligament exists. However, it should also be noted, that truly functional cruciate ligaments exist rarely in knee replacements, and, therefore, the femoral component of the first embodiment should qualify for most knee prosthetic applications. An additional benefit of using the femoral component of the first embodiment is achieved when the femoral component is used in conjunction with a rotating platform type bearing, such is that disclosed in U.S. Pat. No. 4,470,158. With such a combination, the tibia is moved posteriorly, during flexion, thereby causing the quadriceps lever arm for the patella to increase and making the quadriceps apparatus overall more effective.

The first embodiment can be used in conjunction with a fixed-bearing type knee prosthesis, a rotational and translational bearing type knee prosthesis (such as that disclosed in U.S. Pat. No. 5,702,466), a hinged type knee prosthesis, or a posterior stabilized type knee prosthesis. Further, the first embodiment is particularly useful with the posterior stabilized knee prosthesis disclosed in U.S. Provisional Application Ser. No. 60/065,680, filed Nov. 18, 1997 by the inventor herein, and the hinged knee prosthesis disclosed in U.S. application Ser. No. 08/354,480, filed Dec. 12, 1994 wherein the inventor herein is a co-inventor.

The second embodiment of the invention is applicable where one or both cruciate ligaments are to be retained. The second embodiment is formed with the same design principles as the first embodiment but has a shorter primary load bearing segment in the posterior direction as compared with the first embodiment. As such, congruent contact can be maintained between the femoral component of the second embodiment and a bearing insert over a range of normal activity (i.e., typical range of flexion) due to the articulation of the primary load bearing segment and the bearing insert, and, in deep flexion beyond articulation of the primary load bearing segment and the bearing insert, roll back of the femur on the tibia is permitted in a generally natural movement under tension of the retained cruciate ligament(s). Roll back is the combination of sliding translation and rotation.

These and other features of the subject invention will be better understood through a study of the following detailed description and accompanying drawings.

BRIEF DESCRIPTION OF THE DRAWINGS

FIG. 1 is an elevational view showing a prior art femoral component. FIG. 1 is taken from FIG. 39 of U.S. Pat. No. 4,470,158.

FIG. 2 is a side view of the prior art femoral component shown in FIG. 1. FIG. 2 is taken from FIG. 40 of U.S. Pat. No. 4,470,158.

DETAILED DESCRIPTION OF THE PREFERRED EMBODIMENTS

The teachings set forth below have many applications in the field of prosthetics and can be applied to designs of prosthetics for fingers, elbows, and other bone joints. To explain the principles of the invention, the disclosure set forth below is described in terms of a knee joint prosthesis, but this disclosure is no way limited to this single application. Additionally, for illustrative purposes, the subject invention is described below in terms of specific embodiments. As set forth below, the inventive concepts underlying the disclosed embodiments are equally applicable to other embodiments.

Figure 3:
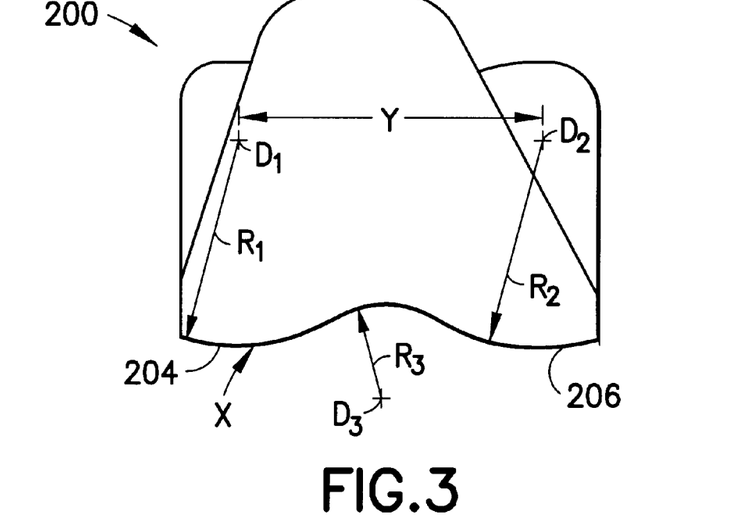
FIG. 3 is a front view of the first embodiment of the femoral component of the subject invention.

Referring generally to FIGS. 3–6, a first embodiment of a femoral component 200 formed in accordance with the subject invention is shown. The femoral component 200 includes an outer bearing surface 202, defined by two condyles 204, 206 and a web 208 extending between and connecting the condyles 204, 206. The shape of the bearing surface 202 is defined by the rotation of a plane curve "X" about three axes, represented by points, M1–M3. The plane curve "X" has a different shape from the prior art plane curve "F", discussed above. Referring to FIG. 3, the shape of the plane curve "X" is generally defined by three radii R1–R3, respectively extending from center points D1–D3. The center points $D_1$ and $D_2$ are spaced apart a distance Y, and point $D_3$ is located along the central axis of the femoral component 200.

Figure 4:
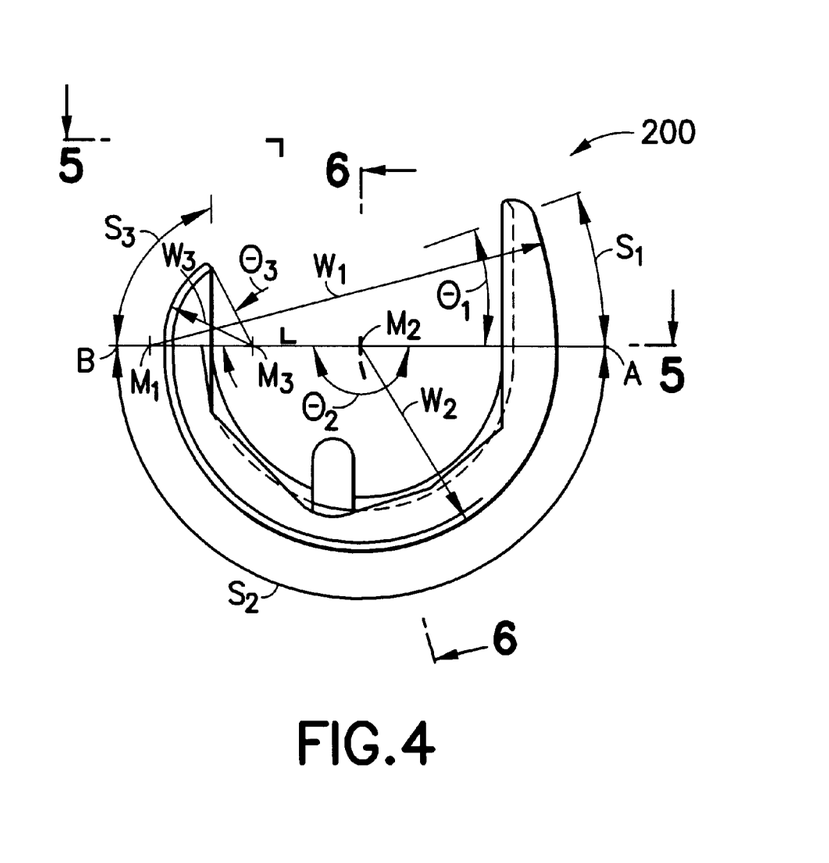
FIG. 4 is a side view of the first embodiment of the femoral component of the subject invention.
Figure 5:
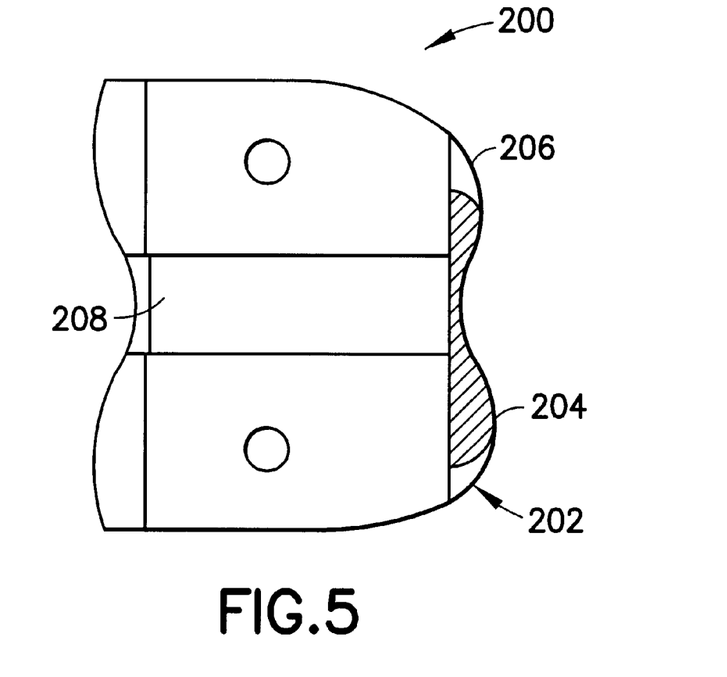
FIG. 5 is a partial cross-sectional view of the first embodiment of the femoral component of the subject invention taken along line 5—5 of FIG. 4.
Figure 6:
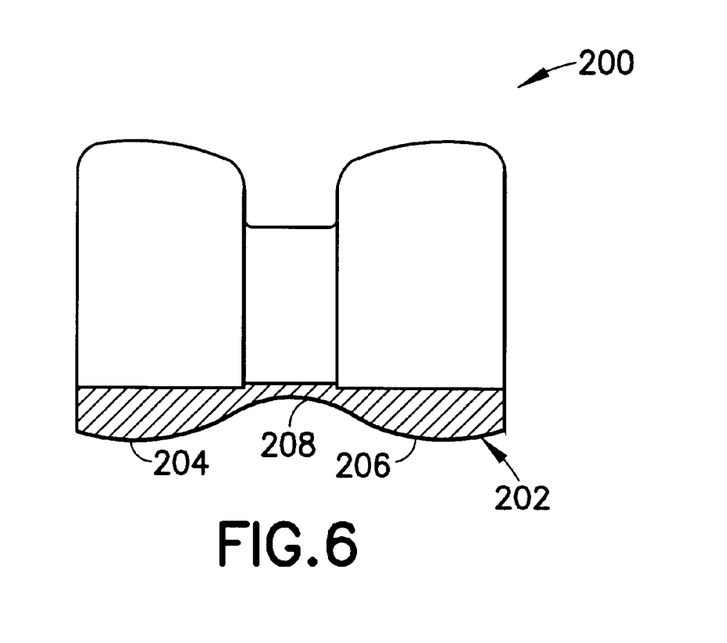
FIG. 6 is a partial cross-sectional view of the first embodiment of the femoral component of the subject invention taken along line 6—6 of FIG. 4.
Figure 7:
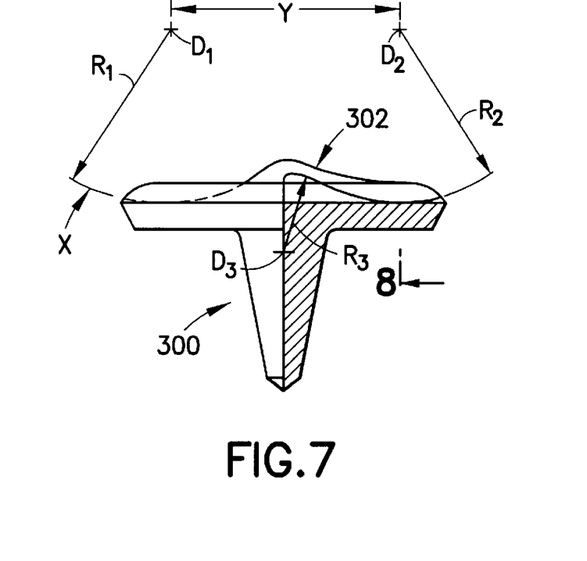
FIG. 7 is an elevational view of a bearing insert.
Figure 8:
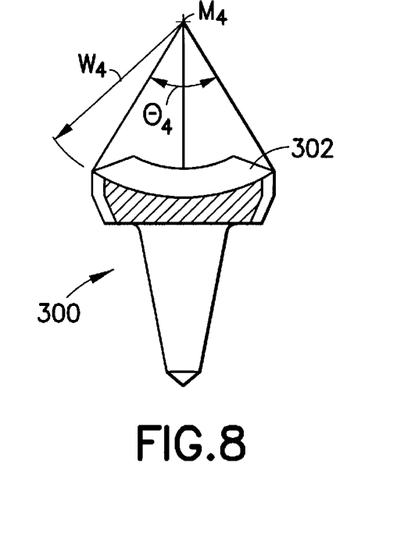
FIG. 8 is a cross-sectional view of the bearing insert taken along line 8—8 of FIG. 7.

As shown in FIG. 4, the profile of the femoral component 200 is generated from the anterior to the posterior of the femoral component 200 by rotating the plane curve "X" about the axes M1–M3 to define a series of segments of surfaces of revolution. The axes M1–M3 can be perpendicular to the plane of FIG. 4 or alternatively be obtuse thereto. Thus, a first segment S1 is defined by rotating the plane curve "X" about the axis M1 an angle θ1 at a radius W1. W1 is the largest generating radius and may be defined at infinity. A second segment S2 extends between points A and B, shown in FIG. 4, and is formed by rotating the plane curve "X" about the axis M2, at a radius W2. Preferably, the radius W2 is equal to the radius R1, which, in turn, is equal to the radius R2. Thus, for each of the condyles 204, 206, the segment S2 is preferably spherically generated about a point on the axis M2. Also, the segment S2 is formed by rotating the plane curve "X" an angle θ2, which is at least 120°, about the axis M2. For example, as shown in FIG. 4, the plane curve "X" can be rotated an angle θ2 of 180° about the axis M2. Additionally, a third segment S3 is defined in the posterior-most portion of the femoral component 200 and is generated by rotating the plane curve "X" an angle θ3 about the axis M3 at a radius W3. The third segment S3 completes the profile of the femoral component 200 by extending from the segment S2 to the posterior-most portion of the femoral component. As is readily apparent, the length of the segment S3 is an inverse function of the length of the segment S2, with an increase in the length of one commensurately causing a decrease in the other. It should be noted, that the radius W2 used to define the spherical surface along the respective segments S2 of the condyles 204, 206 is selected to be preferably less than the radius used to define the segment S2 of the prior art femoral component described above.

Referring to FIGS. 7–8 and 11–12, the femoral component 200 is formed for articular bearing engagement with a bearing insert 300, having a superior bearing surface 302 shaped to articulate with the segment S2 of the femoral component 200. Specifically, the shape of the superior bearing surface 302 is defined by the plane curve "X" being rotated about an axis M4 at a radius W4 over an angle θ4. To achieve congruent articulation between the bearing surface 302 and the segment S2 of the femoral component 200, the radius W4 is equal to the radius W2. In other respects, the generation of the shape of the superior bearing surface 302 is disclosed in U.S. Pat. No. 4,470,158, with respect to the primary load bearing surface 140 of the tibial bearing component 139, and reference is made thereto.

Figure 11:
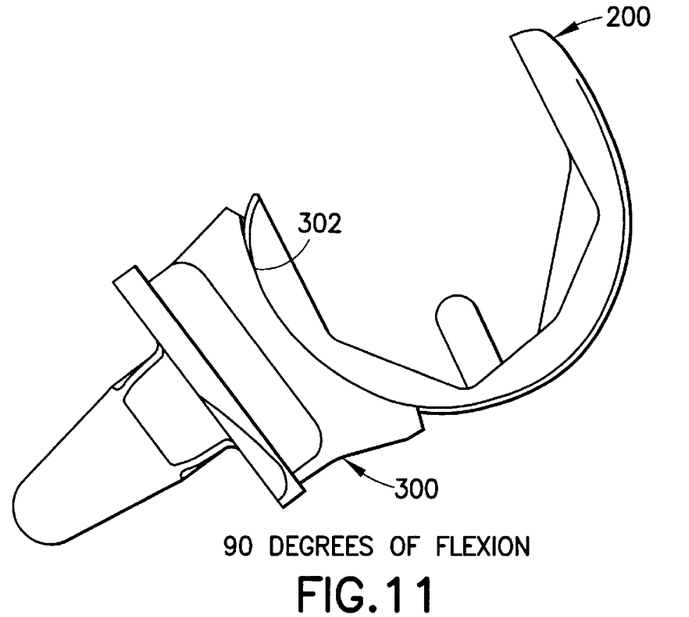
FIG. 11 is a plan view of the first embodiment of the femoral component in 90° of flexion relative to a bearing insert and a tibial component.
Figure 12:
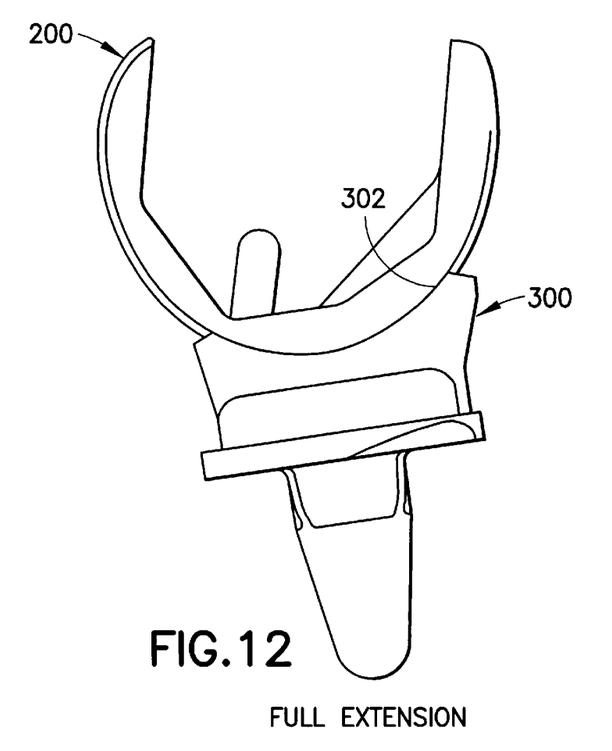
FIG. 12 is a plan view showing the first embodiment of the femoral component in full extension with a bearing insert and a tibial component.

The segment S2 is the primary load bearing segment of the femoral component 200, since the segment S2 is in articular bearing engagement with the superior bearing surface 302 over a range of flexion which corresponds to the majority of normal knee movement, such as that during walking, standing, running, and sitting. Specifically, with the femoral component 200 being in articular bearing engagement with the bearing insert 300, the femoral component 200 provides a wearer of the component 200 a range of motion extending from full extension (0° of flexion) to at least 45° of flexion and up to approximately 105° of flexion where the substantially same contact configuration is maintained between the femoral component 200 and the bearing insert 300. Consequently, the femoral component 200 may define the substantially same contact configuration with the bearing insert 300 in full extension, as shown in FIG. 12, as well as at 90° of flexion, as shown in FIG. 11. Where there is point or line articulation between the segment S2 and the bearing insert 300 (i.e., the radius W4 does not equal the radius W2), the segment S2 still articulates with the bearing insert 300 over the majority of a wearer's activity. Also, the substantially same contact configuration is also still maintained over a range of at least 45° of flexion and up to 105° of flexion between the surfaces. The maintenance of the substantially same contact configuration over a greater range of flexion than in the prior art reduces contact stress and wear.

Figure 9:
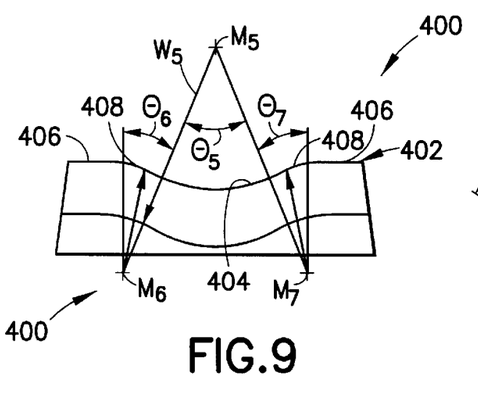
FIG. 9 is an elevational view of a patella component.
Figure 10:
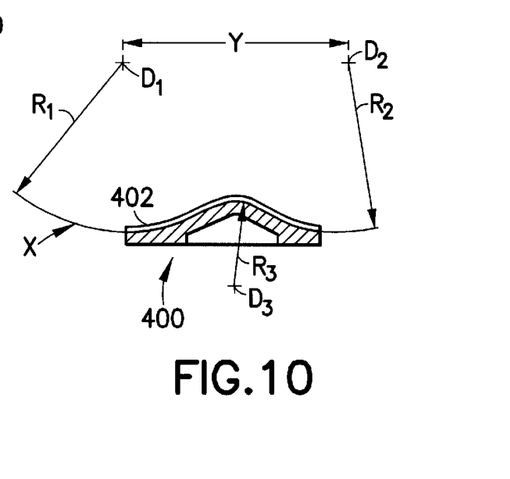
FIG. 10 is a view of a representative cross-section of the patella component of FIG. 9.

A patella component 400 can also be used with the femoral component 200. Referring to FIGS. 9–10, the patella component 400 is shown. The patella component is formed with a bearing surface 402. To achieve congruent articulation with the segment S2 of the femoral component 200, the bearing surface 402 is shaped by rotating the plane curve "X" about the axis M5 for an angle θ5 at a radius W5, where the radius W5 equals the radius W2. The axis M5 is located centrally relative to the length of the patella component 400, so that the rotation of the plane curve "X" as described above defines a central bearing surface 404. In operation, the central bearing surface 404 will congruently articulate with the segment S2. Outer portions 406 of the bearing surface 402 may be formed to congruently articulate with the segment S1, as taught in U.S. Pat. No. 4,470,158, to be generated at the same radius as the radius W1. Transitional bearing surfaces 408, having parameters M6, M7, θ6 and θ7, are formed in accordance with U.S. Pat. No. 4,470,158. In all other respects, the patella component 400 is like the patella bearing component 109 of U.S. Pat. No. 4,470,158. The bearing surface 402 need not be formed to congruently articulate with any portion of the femoral component 200.

Although the femoral component is described above as having three of the segments S1–S3, the actual number of the segments is not a critical feature of the subject invention. For example, the primary load bearing segment S2 can be formed by the plane curve "X" to extend about the entire femoral component 200, wherein the segment S2 would be defined by continuous spherical surfaces throughout the length thereof. Alternatively, different shaped plane curves, such as the plane curve "F", described above with respect to the prior art, may be utilized. The critical feature of the invention is that the substantially same contact configuration is maintained between the primary load bearing segment S2 and the bearing insert 300 over a range of motion extending from 0° of flexion to at least 45° of flexion and up to approximately 105° of flexion. As is readily apparent, the maintenance of the substantially same contact configuration is not a function of the number of segments defining the shape of the femoral component 200, but, rather the actual shapes of the contacting surfaces. The plane curve "X" can be rotated about any number of generating axes to define the shape of the femoral component 200. It is critical, though, that one of the segments which is defined will be a primary load bearing segment formed to maintain substantially the same contact configuration over a range of 0° of flexion to at least 45° of flexion and up to 105° of flexion with respect to the bearing insert 300. The lower limit of the specified range can be specified to be at least 60° of flexion. Furthermore, the subject femoral component is configured to accommodate two (2) articulations which use the primary load bearing segments, and wherein one of these articulations does not change over a range of at least 0° of flexion to at least 45° of flexion.

The first embodiment of the subject invention is not intended for use in replacing a natural knee joint where the cruciate ligaments are viable. Rather, the first embodiment is to be used where the cruciate ligaments are sacrificed or incompetent. It should be noted that the subject invention does not model natural knee movement. However, since the invention is for use where cruciate ligaments are not viable, the invention is not restricted to following natural knee movement. Without such restriction, the invention advantageously allows for greater congruent contact, and thus less wear, without a loss in function as compared with prior art designs, especially those designed for use with viable cruciate ligaments. It should also be noted that in the majority of knee replacement cases, the cruciate ligaments are not viable, and, therefore, the subject invention is applicable in most knee replacement cases.

Figure 13:
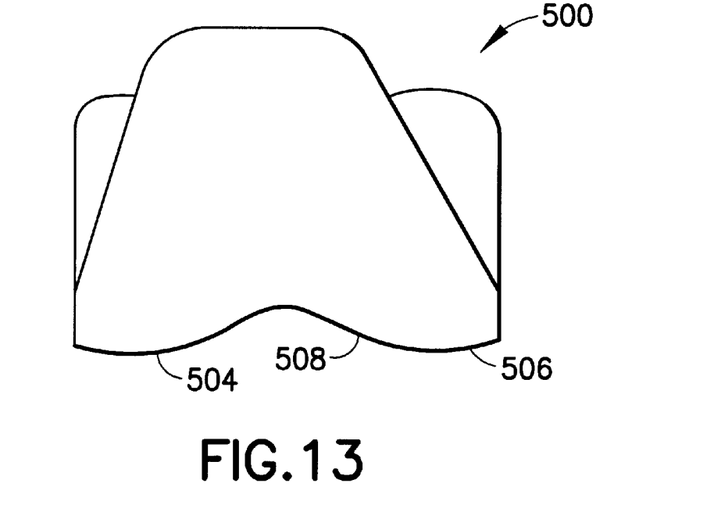
FIG. 13 is a front view of the second embodiment of the femoral component of the subject invention.
Figure 14:
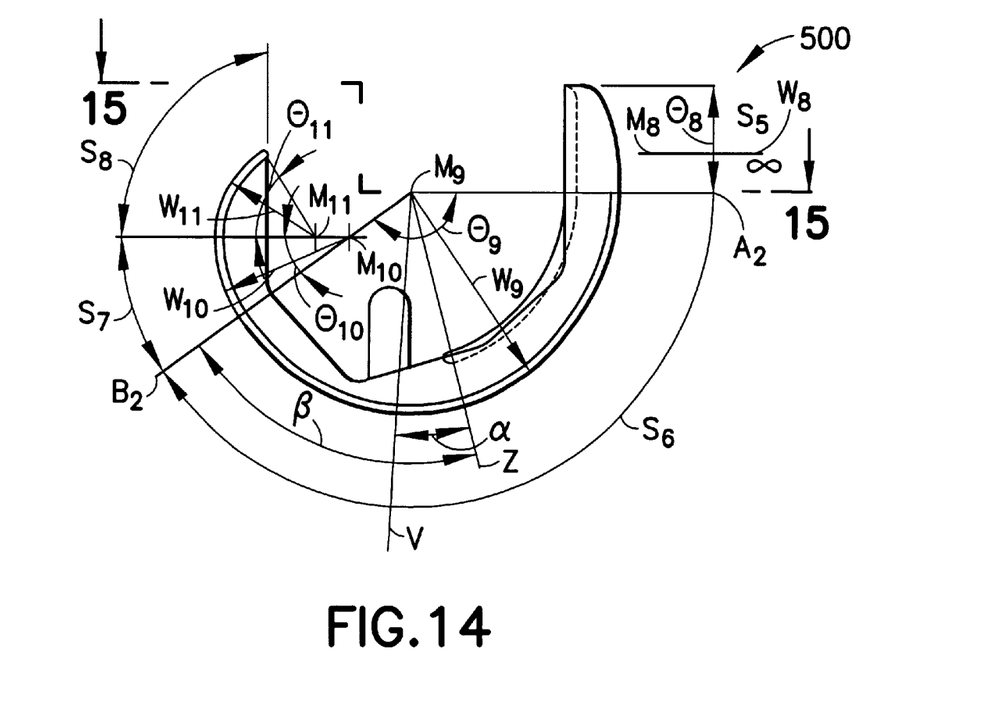
FIG. 14 is a side view of the second embodiment of the femoral component of the subject invention.
Figure 15:
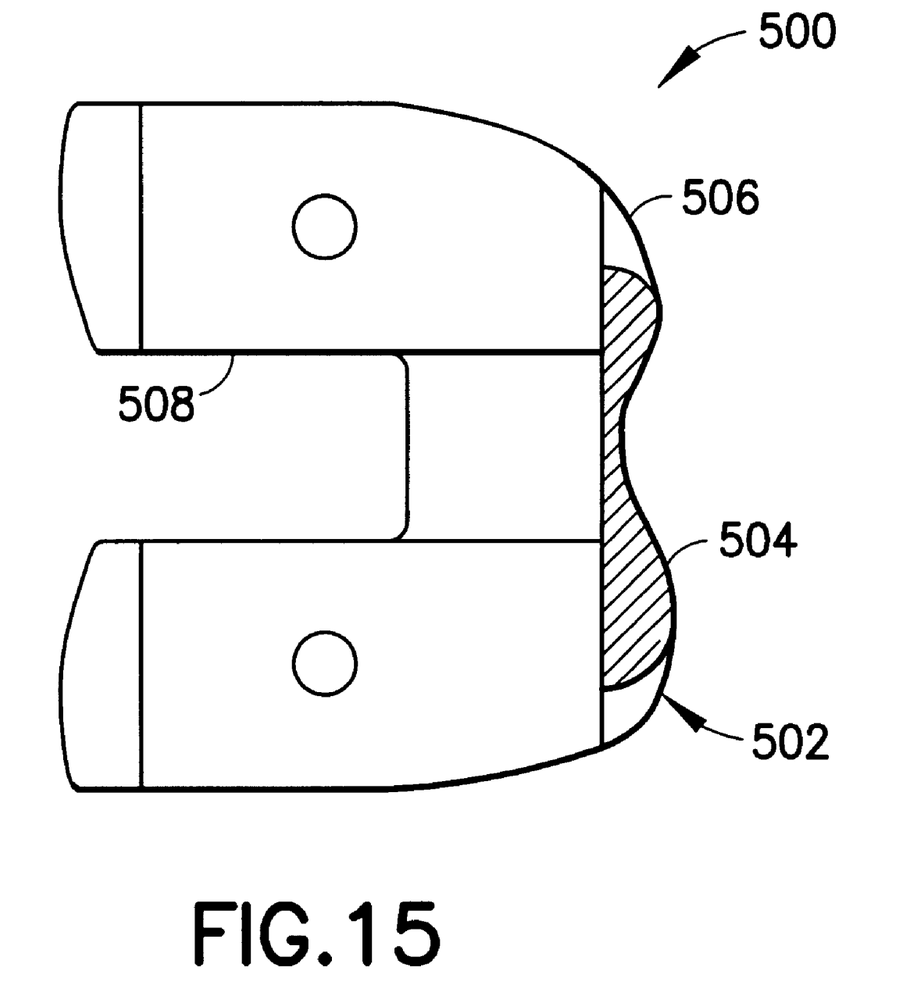
FIG. 15 is a partial cross-sectional view of the second embodiment of the femoral component of the subject invention taken along line 15—15 of FIG. 14.

Referring to FIGS. 13–15, a second embodiment of a femoral component is shown and generally designated with the reference numeral 500. As with the first embodiment described above, the femoral component 500 includes an outer bearing surface 502, defined by two condyles 504, 506. In contrast to the first embodiment, the femoral component 500 is formed with a cruciate ligament notch 508 extending from the posterior of the femoral component 500 and between the condyles 504, 506, to have a sufficient length to accommodate retained cruciate ligament(s).

The plane curve "X" described above is used to define the bearing surface 502. As shown in FIG. 14, the plane curve "X" is rotated about four axes, M8–M11. In particular, the plane curve "X" sweeps a first segment S5 at a radius W8 over an angle of θ8. It is preferred that the radius W8 equal infinity, wherein the plane curve "X" is moved along a straight path defined by moving linearly the axis M8 with the angle θ8 actually indicating linear displacement, rather than angular displacement. The plane curve "X" is further swept about the axis M9 at a radius W9 for an angle of θ9 to define a primary load bearing segment S6 of the femoral component 500. To define the segment S6 with spherical surfaces, the radius W9 equals both of the radii R1 and R2 of the plane curve "X". As shown in FIG. 14, the primary load bearing segment S6 extends between axis A2 and axis B2. It is preferred that the angle θ9 equal 146°. It is also preferred that the axis B2 be fixed relative to a vertical axis V of the femoral component 500. Referring to FIG. 14, a reference axis Z is defined at an angle α relative to the vertical axis V. Preferably, the angle α equals 15° which is equal to the typical angular offset between the longitudinal axes of the natural femur and tibia as measured in an anterior-posterior direction. The reference axis Z and the axis B2 subtend an angle β, which is preferably 71°. A segment S7 extends posteriorly from the segment S6, and is defined by a radius W10 rotated about the axis M10 for an angle of θ10. A segment S8 completes the shape of the bearing surface 502 and is defined about the axis M11 at a radius of W11 rotated for an angle of θ11.

The segments S5, S7 and S8 are generally formed in the same manner as the segments S1, S3 and S4 as disclosed in U.S. Pat. No. 4,470,158. The primary load bearing segment S6, however, is defined differently than the prior art. By defining the primary load bearing segment S6 as described above, the primary load bearing segment S6 can maintain the substantially same contact configuration with the bearing surface 302 of the bearing insert 300, described above, over a range of at least 45° of flexion and up to approximately 105° of flexion.

The primary load bearing segment S6 is preferably formed to congruently articulate with a superior bearing surface of a meniscal bearing, such as that disclosed in U.S. Pat. Nos. 4,309,778 and 4,340,978. The superior bearing surface of the meniscal bearing is formed like the superior bearing surface 302 of the bearing 300, described above, with congruent articulation being achieved between the primary load bearing segment S6 and the superior bearing surface 302 by setting the radius W4 equal to the radius W9. However, congruent articulation is not required to achieve the objective of the invention. With respect to the segments S7 and S8, there is no congruent articulation with the superior bearing surface 302 (i.e., the radii W10 and W11 should not equal the radius W4). Unlike the first embodiment, the femoral component 500 is formed to follow the natural movement of a human knee and allow for roll back of the femur relative to the tibia in deep flexion. The location of the axis B2 limits posteriorly the congruent articulation between the femoral component 500 and the meniscal bearing, with point or line contact being formed therebetween over the segments S7 and S8. It should be noted that congruent articulation inhibits the natural roll back movement of the femur relative to the tibia. With at least one cruciate ligament being retained, the naturally created force for roll back generated by the cruciate ligament or ligaments makes use of the meniscal bearing to create anterior-posterior translation. Additionally, the femoral component 500 is formed to articulate with the patellar component 400 in the same manner as described with respect to the first embodiment.

The femoral component 500 is intended to achieve the object of the invention as described above with respect to the first embodiment. The femoral component 500 can be modified in all the same manners as the first embodiment so long as incongruent articulation is provided in deep flexion.

As is readily apparent, numerous modifications and changes may readily occur to those skilled in the art, and hence it is not desired to limit the invention to the exact construction and operation shown and described. Accordingly, all suitable modification equivalents may be resorted to falling within the scope of the invention as claimed.

What is claimed is:

1. A prosthetic joint for replacement of a natural bone joint, said prosthetic joint comprising:
   a first prosthetic component having a first superior bearing surface, at least a portion of said first superior bearing surface defining a primary load bearing segment;
   a second prosthetic having a second superior bearing surface in articulation with said primary load bearing segment; and
   a third prosthetic component having a third superior bearing surface in articular bearing engagement with said primary load bearing segment, wherein said primary load bearing segment is formed to constantly maintain a substantially same contact configuration with said third superior bearing surface over a range of articulation extending from 0° of flexion to up to 105° of flexion.

2. A prosthetic joint as in claim 1, wherein said third superior bearing surface is in congruent articulation with said primary load bearing segment over said range of articulation.

3. A prosthetic joint as in claim 1, wherein said first superior bearing surface is a smooth, continuous surface formed by a series of segments of surfaces of revolution, the respective shapes of which are generated by rotating a common generating curve around a plurality of separate generating axes at respective pairs of major generating radii and through respective angles of rotation, the largest segment of these surfaces of revolution being the primary load bearing segment.

4. A prosthetic joint as in claim 3, wherein said primary load bearing segment is generated by rotating said common generating curve at least 120° about one of said generating axes.

5. A prosthetic joint as in claim 3, wherein there are three segments.

6. A prosthetic joint as in claim 1, wherein the prosthetic joint is formed for replacement of a natural knee joint, the first component being a femoral component, the second component being a patella component, and the third component being a bearing insert.

7. A prosthetic joint as in claim 6, wherein the cruciate ligaments of the natural knee joint are not viable.

8. A prosthetic joint as in claim 6, wherein the first component is formed to define two spaced-apart condyles, said condyles at least partially defining said first superior bearing surface, said condyles being connected by a web extending substantially coextensively therewith.

9. A prosthetic joint for replacement of a natural bone joint, said prosthetic joint for articulating with a natural bone in proximity to the natural bone joint, said prosthetic joint comprising:
   a first prosthetic component having a first superior bearing surface, at least a portion of said first superior bearing surface defining a primary load bearing segment, said primary load bearing segment being in articulation with the natural bone; and
   a second prosthetic component having a second superior bearing surface in articular bearing engagement with said primary load bearing segment, wherein said primary load bearing segment is formed to constantly maintain a substantially same contact configuration with said second superior bearing surface over a range of articulation extending from 0° of flexion to up to 105° of flexion.

10. A prosthetic joint as in claim 9, wherein said second superior bearing surface is in congruent articulation with said primary load bearing segment over said range of articulation.

11. A prosthetic joint as in claim 9, wherein said first superior bearing surface is a smooth, continuous surface formed by a series of segments of surfaces of revolution, the respective shapes of which are generated by rotating a common generating curve around a plurality of separate generating axes at respective pairs of major generating radii and through respective angles of rotation, the largest segment of these surfaces of revolution being the primary load bearing segment.

12. A prosthetic joint as in claim 11, wherein said primary load bearing segment is generated by rotating said common generating curve at least 120° about one of said generating axes.

13. A prosthetic joint as in claim 11, wherein there are three segments.

14. A prosthetic joint as in claim 9, wherein the joint is formed for replacement of a natural knee joint, the natural bone being a patella, the first component being a femoral component, and the second component being a bearing insert.

15. A prosthetic joint as in claim 14, wherein the cruciate ligaments of the natural knee joint are not viable.

16. A prosthetic joint as in claim 14, wherein the first component is formed to define two spaced-apart condyles, said condyles at least partially defining said first superior bearing surface, said condyles being connected by a web extending substantially coextensively therewith.

* * * * *